United States Patent
Den Heeten et al.

(10) Patent No.: US 9,826,950 B2
(45) Date of Patent: Nov. 28, 2017

(54) MAMMOGRAPHY APPARATUS AND METHOD TO ADJUST OR TUNE THE MECHANICAL SETTINGS OF SUCH A MAMMOGRAPHY APPARATUS

(71) Applicant: Academisch Medisch Centrum bij de Universiteit van Amsterdam, Amsterdam (NL)

(72) Inventors: Gerardus Johannes Den Heeten, Amsterdam (NL); Cornelis Antonius Grimbergen, Amsterdam (NL); Christiaan Neeleman, Veldhoven (NL)

(73) Assignee: Academisch Medisch Centrum bij de Universiteit van Amsterdam, Amsterdam (NL)

( * ) Notice: Subject to any disclaimer, the term of this patent is extended or adjusted under 35 U.S.C. 154(b) by 326 days.

(21) Appl. No.: 14/524,806

(22) Filed: Oct. 27, 2014

(65) Prior Publication Data
US 2015/0043711 A1 Feb. 12, 2015

Related U.S. Application Data

(63) Continuation of application No. PCT/NL2013/050283, filed on Apr. 18, 2013.

(30) Foreign Application Priority Data

Apr. 27, 2012 (NL) .................... 2008727

(51) Int. Cl.
*A61B 6/04* (2006.01)
*A61B 6/10* (2006.01)
(Continued)

(52) U.S. Cl.
CPC ............... *A61B 6/502* (2013.01); *A61B 6/04* (2013.01); *A61B 6/0407* (2013.01);
(Continued)

(58) Field of Classification Search
CPC ........... A61B 6/00; A61B 6/04; A61B 6/0407; A61B 6/0414; A61B 6/0442; A61B 6/10;
(Continued)

(56) References Cited

U.S. PATENT DOCUMENTS 5,099,503 A 3/1992 Strommer
5,355,715 A 10/1994 Rausche et al.
(Continued)

FOREIGN PATENT DOCUMENTS

WO 2011/102713 8/2011
WO 2013/162357 10/2013

*Primary Examiner* — Anastasia Midkiff
(74) *Attorney, Agent, or Firm* — Peacock Myers, P.C.; Jeffrey D. Myers

(57) ABSTRACT

A method to adjust or tune mechanical settings of a mammography apparatus comprising an x-ray source, a paddle and a detector with a detector cover, wherein before executing an x-ray measurement a patient's breast is placed and compressed between the detector cover and the paddle, wherein prior to the x-ray measurement reaction forces between the mammography apparatus and the patient's breast are minimized. The invention relates further to a mammography apparatus comprising an x-ray source, a paddle and a detector with a detector cover, which apparatus is provided with at least one weighing means to measure the downwards forces exerted by (the part of) the apparatus above the weighing means towards the ground.

4 Claims, 2 Drawing Sheets

(51) Int. Cl.
*H05G 1/02* (2006.01)
*A61B 6/00* (2006.01)
*A61B 90/17* (2016.01)
*A61B 90/00* (2016.01)
*G01G 19/52* (2006.01)
*G01G 19/00* (2006.01)

(52) U.S. Cl.
CPC .............. *A61B 6/0414* (2013.01); *A61B 6/10* (2013.01); *A61B 90/17* (2016.02); *A61B 2090/033* (2016.02); *A61B 2090/034* (2016.02); *A61B 2090/036* (2016.02); *A61B 2090/064* (2016.02); *A61B 2090/065* (2016.02); *A61B 2576/02* (2013.01); *F04C 2270/041* (2013.01); *G01G 19/00* (2013.01); *G01G 19/52* (2013.01); *H05G 1/02* (2013.01)

(58) Field of Classification Search
CPC .. A61B 6/40; A61B 6/50; A61B 6/502; A61B 50/00; A61B 90/00; A61B 90/03; A61B 90/033; A61B 90/034; A61B 90/036; A61B 90/06; A61B 90/064; A61B 90/065; A61B 90/17; A61B 2560/00; A61B 2560/02; A61B 2560/0266; A61B 2560/04; A61B 2560/0406; A61B 2560/16; A61B 2560/164; A61B 2576/00; A61B 2576/02; H05G 1/00; H05G 1/02; H05G 1/26; H05G 1/30
See application file for complete search history.

(56) References Cited

U.S. PATENT DOCUMENTS

| | | |
|---|---|---|
| 5,590,166 A | 12/1996 | Suni et al. |
| 6,049,583 A | 4/2000 | Galkin et al. |
| 7,558,367 B1 | 7/2009 | Tinwala et al. |
| 2006/0245541 A1 | 11/2006 | Aubel |
| 2007/0121782 A1* | 5/2007 | Sendai ................ A61B 6/0414 378/37 |
| 2009/0262887 A1 | 10/2009 | Iordache et al. |
| 2009/0304146 A1 | 12/2009 | Ramsauer |
| 2014/0328458 A1* | 11/2014 | Erhard ................ A61B 6/0414 378/37 |

* cited by examiner

MAMMOGRAPHY APPARATUS AND METHOD TO ADJUST OR TUNE THE MECHANICAL SETTINGS OF SUCH A MAMMOGRAPHY APPARATUS

CROSS-REFERENCE TO RELATED APPLICATIONS

This application is a continuation application of Patent Cooperation Treaty Application No. PCT/NL2013/050283, entitled "Mammography Apparatus and Method to Adjust or Tune the Mechanical Settings of Such a Mammography Apparatus", filed on Apr. 18, 2013, which claims priority to Netherlands Patent Application No. 2008727, filed on Apr. 27, 2012, and the specifications and claims thereof are incorporated herein by reference.

BACKGROUND OF THE INVENTION

Field of the Invention (Technical Field)

The present invention relates to a method to adjust or tune mechanical settings of a mammography apparatus. The invention further relates to such a mammography apparatus.

Description of Related Art

WO2011/102713 discloses a mammography apparatus comprising an x-ray source, a paddle and a detector with a detector cover. The known mammography apparatus is floorstanding and comprises a mainframe that supports a subframe in which the x-ray source, the paddle and the detector are mounted. In such a known mammography apparatus it is day to day practice to place and compress a patient's breast between the detector and the paddle before executing an x-ray measurement in order to optimize the image quality and minimize the required x-ray doses. During the procedure the patient is standing next to the mammograph. The compression is applied by bringing the patient's breast in between the x-ray detector and the paddle, which paddle can thereafter be lowered in the direction and relative to the detector by hand or by activating a motor built in the mammography apparatus. It is commonly known that this procedure may inflict serious pain on the patient.

US2006/0245541 discloses a floorstanding mammography apparatus comprising a mainframe in which a subframe is mounted that supports an x-ray source, a paddle and a detector with a detector cover, wherein before executing an x-ray measurement a patients breast is placed and compressed between the detector cover and the paddle. This document acknowledges the pain experienced by a patient and teaches to reduce this pain by first positioning the breast on the detector cover, then move the paddle down to obtain less than full desired compression, followed by moving the detector cover up until the full desired compression is achieved. As a result the level of the shearing and compressive forces exerted on the breast will be more distributed and balanced. A problem of this known solution is that the size and types of patient's breasts vary so considerably that the required distance of movement of the detector cover and the paddle varies. Another point of variation is that a technician must determine the required compression for each individual breast, which is done through training and experience. Based on his training and experience the technician must determine the movement of the paddle and the subsequent movement of the detector cover to obtain the full desired compression of the breast. It goes without saying that in practice the results of this known operator-dependent method will be most of the time suboptimal in terms of pain experienced by the patient, and far from reproducible.

BRIEF SUMMARY OF THE INVENTION

It is one of the objectives of the invention to further reduce the above-described experience of pain.

It is another objective of the invention to improve the reliability and repeatability of the x-ray measurement by providing a more reliable compression of the breast.

It is still another objective of the invention to provide an improved mammography apparatus which ensures that the objectives of reduced pain and more reliable and repeatable x-ray measurements can be achieved.

These and other objectives of the invention which will become apparent from the following disclosure, are attained with the method and mammography apparatus according to one or more of the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
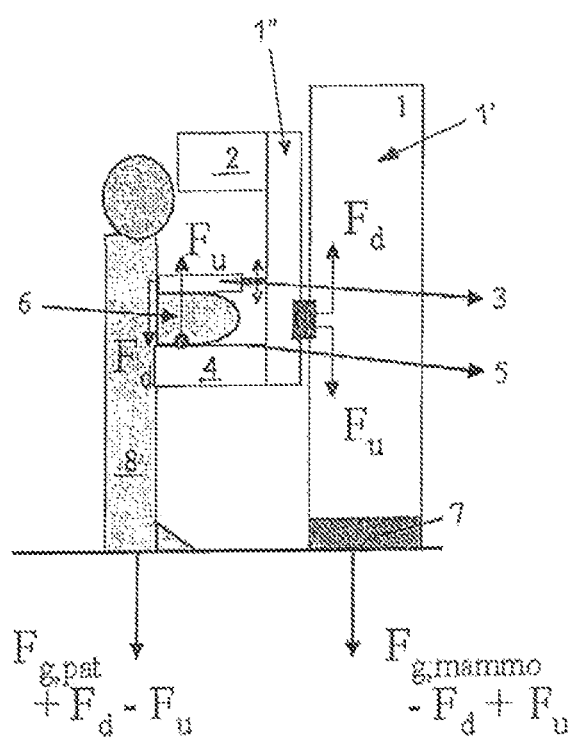
FIG. 1 is a schematic diagram of the apparatus of the present invention.

According to a first aspect of the invention at least prior to the x-ray measurement a first upward force applied by the detector cover on the patient's breast is measured and a second downward force applied by the paddle on the patient's breast is measured, which first and second measured forces are subsequently balanced during the compression of the breast so as to minimize reaction forces between the paddle, the detection cover and the patient.

Essential for the invention is the actual measurement of the upward and downward forces applied to the breast, since it is found that for an optimal compression of the breast, the reaction forces between the mammography apparatus and the patient should be minimized as reaction forces are at the expense of the forces available for flattening of the breast tissue and may lead to undesirable stretching of the skin that may cause additional pain during the measurement procedure. The method of the invention results in an accurate measurement of the compression forces applied to the individual breast which is also beneficial for the accuracy and repeatability of the x-ray measurement.

Preferably weighing means are provided for measuring the first upward force applied by the detector cover on the patient's breast, which weighing means are applied in or under the mainframe to measure downwards forces exerted by the mammography apparatus or by part of said apparatus towards the floor, and which weighing means are used for measuring the weight exerted by the mammography apparatus or by part of said apparatus when the patient's breast is lifted by the detector cover, followed by subtracting therefrom the weight measured by the weighing means when the detector cover is unloaded. This provides a straightforward and reliable measurement of the first upward force taking into account the additional force caused by the stretching of the skin and breast tissue during the lifting of the breast.

It is remarked that U.S. Pat. No. 6,049,583 discloses a mammography apparatus comprising a mainframe and a subframe mounted in the mainframe and supporting an x-ray source, a paddle and a detector with a detector cover, which is provided with means to monitor a compression force applied to a breast. These known means to monitor a compression force are mounted in a body to which the compression force is applied and which is placed between the detector cover and the paddle. These means for measuring the compression force are neither suited nor intended for use in measuring the upward and downward forces as applied to the breast before the x-ray measurement.

Preferably the difference between the first upward force applied by the detector cover on the breast, and the second downward force applied by the paddle on the patient's breast is measured by another or the same weighing means which is arranged in or under the mainframe to measure forces exerted by the mammography apparatus or part of said apparatus towards the floor, and which measurement is executed during the breast being compressed between the paddle and the detector cover, by measuring with said weighing means the weight exerted by the mammography apparatus or by part of said apparatus, and that this measurement of the weight is compensated with the weight measured by the weighing means when the detector cover is unloaded, that is when no patient is present. During the compression part of the exerted compression force will be taken up by the interaction of the paddle with the skin of the patient. This part of the applied compression force is recorded by the weighing measurement by a reduction of the measured weight; the interaction of the paddle with the skin is delivering a lifting force to the mammograph that is recorded with the weighing means.

According to the method of the invention it is further possible and occasionally preferable while maintaining the compression forces exerted by the detection cover and the paddle on the breast by fixing their mutual distance, that the detection cover and the paddle are simultaneously moved in their vertical position to balance the first upward force exerted on the breast by the detector cover and the second downward force exerted on the skin of the breast by the paddle until these forces substantially have the same value. This means that with the compression that is applied to the breast during the x-ray measurement the reaction forces interacting between the mammograph and the patient are minimized such that a balanced position of the breast tissue is approached as much as possible. This arranges that the x-ray measurement is done with a compression force which is optimized for breast flattening only. Further, a reduction in pain and discomfort is thus achieved for the patient.

The benefits of the invention can be achieved with a mammography apparatus comprising an x-ray source, a paddle and a detector with a detector cover, wherein according to the invention the apparatus is provided with at least one weighing means to measure the downward forces exerted by the apparatus or by part of the apparatus above the weighing means, which forces are directed towards the floor. The mammography apparatus may be suspended from a ceiling, or maybe a floorstanding mammography apparatus.

The weighing means may form part of the mammography apparatus of the invention and, in case of a floorstanding mammography apparatus, may be placed somewhere in its foot. According to the invention it is also possible to provide an arrangement of a mammography apparatus and a weighing means, wherein the weighing means is separate yet supports the mammography apparatus.

Figure 2:
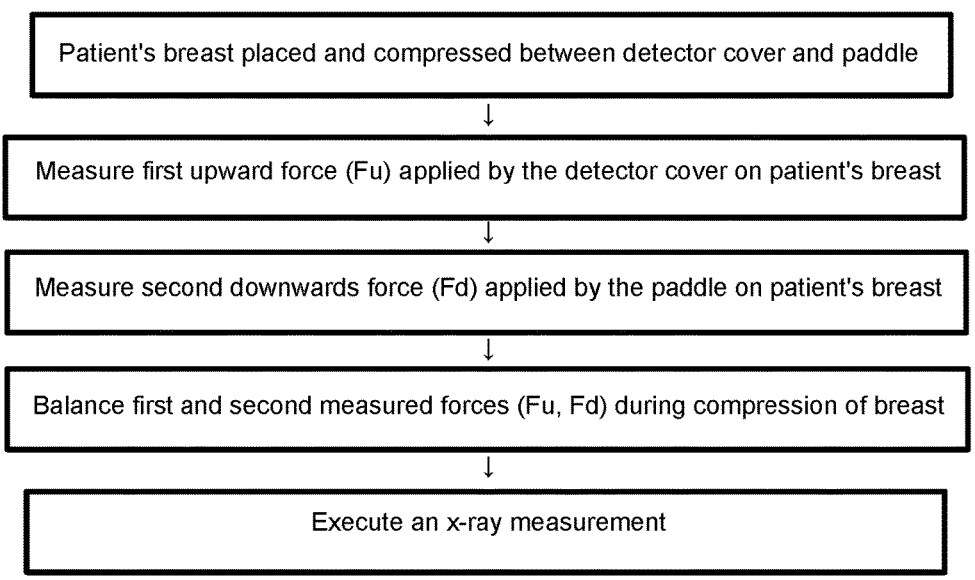
FIG. 2 is a flow diagram of the method of the present invention.

The invention will hereinafter be further elucidated with reference to a schematic drawing of a single (FIG. 1) showing a patient standing next to a mammography apparatus according to the invention and to a flow diagram of a single figure (FIG. 2) directed to the method according to the invention.

The mammography apparatus of the invention is generally denoted with reference 1. This mammography apparatus 1 has a mainframe 1' that is provided with an x-ray source 2, a paddle 3 and a detector 4 with a detector cover 5 that contacts the underside of a patient's breast 6. The person skilled in the art is aware that the x-ray source 2, the paddle 3 and the detector 4 are placed on a subframe 1" (also called c-arm) that is mounted in the mainframe 1'.

The mammography apparatus 1 shown in this exemplary embodiment of the invention is provided with a weighing scale 7 in the foot of the mammography apparatus 1, which weighing scale 7 registers the downward force exerted by the mammography apparatus 1 towards the floor. It is of course also possible to place the weighing scale higher in the foot of the mammography apparatus 1 as long as both the detector 4 and the paddle 3 reside above the weighing scale in order to be able to monitor the effects of interactions of the patient with the detector 4 and the paddle 3 on the weight measured by this weighing scale.

The patient 8 is standing next to the mammography apparatus 1 and exerts his own weight due to gravity by his feet standing on the floor. This force due to the patient's weight is supplemented with a downward force Fd caused by the compression of the breast 6 by the paddle 3 and diminished by an upward force Fu due to lifting of the breast 6 by the detector cover 5.

According to the invention the mechanical settings of the detector 4 and paddle 3 of the mammography apparatus 1 are adjusted or tuned before executing an x-ray measurement. In doing so the purpose is to minimize reaction forces between the detector cover 5 and the paddle 3 of the mammography apparatus 1 and the patient, particularly the patient's breast 6. For this purpose the patient's breast 6 is first placed on the detector cover 5 and then compressed between the detector cover 5 and the paddle 3. In this process the upward force Fu applied by the detector cover 5 on the patient's breast 6 is measured and the downward force Fd applied by the paddle 3 on the skin of the patient's breast 6 is measured, which forces are balanced during the compression of the breast 6.

The upward force Fu applied by the detector cover 5 on the patient's breast 6 is measured by the weighing means 7 which is arranged to measure downward forces exerted by the mammography apparatus 1 towards the floor, which weighing is done by subtracting the weight measured by the weighing means when the patient is not present and the detector cover is unloaded, from the measured weight exerted by the mammography apparatus 1 when the patient's breast 6 is lifted by the detector cover 5.

Thereafter the difference between the first upward force Fu and the second downwards force Fd applied by the paddle 3 on the patient's breast 6 is measured by (preferably the same) weighing means 7 which is arranged in or under the mainframe to measure forces exerted by the mammography apparatus 1 or part of said apparatus 1 towards the floor, which measurement is executed after the breast 6 is compressed between the paddle 3 and the detector cover 5, by measuring with said weighing means 7 the weight exerted by the mammography apparatus 1 or by part of said apparatus 1, and by compensating this measurement of the weight with the weight measured by the weighing means 7 when the detector cover 5 is unloaded, that is when the patient is absent.

It is further preferable while maintaining the compression forces exerted by the detection cover 5 and the paddle 3 on the breast 6 by fixating their mutual distance, that the detection cover 5 and the paddle 3 are simultaneously moved in their vertical position to balance the upward force Fu exerted on the breast 6 by the detector cover 5 and the downward force exerted on the skin of the breast 6 by the paddle 4 until these forces substantially have the same scalar value. This results into the most balanced posture of the breast 6 while being compressed and provides the best prevention of pain sensations caused by improper stretching of the skin of the breast that does not contribute to its flattening. In connection with further reducing said pain sensations it is beneficial to provide the paddle and/or the detector cover with surface material that reduces friction with the patient's skin.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method to adjust or tune mechanical settings of a floorstanding mammography apparatus comprising a mainframe in which a subframe is mounted that supports an x-ray source, a paddle and a detector with a detector cover, wherein before executing an x-ray measurement a patient's breast is placed and compressed between the detector cover and the paddle, wherein at least prior to the x-ray measurement a first upward force (Fu) applied by the detector cover on the patient's breast is measured, and further a second downwards force (Fd) applied by the paddle on the patient's breast is measured, which first and second measured forces (Fu, Fd) are subsequently balanced during the compression of the breast so as to minimize reaction forces between the paddle, the detection cover and the patient.

2. The method according to claim 1, wherein the first upward force (Fu) applied by the detector cover on the patient's breast is measured by a weighing means which is arranged in or under the mainframe to measure forces exerted by the mammography apparatus or part of said apparatus towards the floor, which weighing means is used for measuring the force exerted by the mammography apparatus or part of said apparatus when the patient's breast is lifted by the detector cover and subtracting therefrom the force measured by the weighing means when the detector cover is unloaded.

3. The method according to claim 1, wherein the difference between the first upward force (Fu) and the second downwards force (Fd) applied by the paddle on the patient's breast is measured by a weighing means which is arranged in or under the mainframe to measure forces exerted by the mammography apparatus or part of said apparatus towards the floor, which measurement is executed after the breast is compressed between the paddle and the detector cover, by measuring with said weighing means the force exerted by the mammography apparatus or by part of said apparatus, and that this measurement of the weight is compensated with the force measured by the weighing means when the detector cover is unloaded.

4. The method according to claim 1, wherein while maintaining the compression forces exerted by the detection cover and the paddle on the breast by fixating their mutual distance, the detector cover and the paddle are simultaneously moved in their vertical positions to balance the first upward force (Fu) exerted on the breast by the detector cover and the second downward force (Fd) exerted on the breast skin by the paddle until these forces substantially have the same value.

* * * * *